United States Patent [19]
Schmidt

[11] Patent Number: 5,019,713
[45] Date of Patent: May 28, 1991

[54] RADIATION THERAPY DEVICE WITH MOVEABLE APERTURE PLATE

[75] Inventor: Ernst-Ludwig Schmidt, Kaiserslautern-Dansenberg, Fed. Rep. of Germany

[73] Assignee: Siemens Medical Laboratories, Inc., Concord, Calif.

[21] Appl. No.: 506,975

[22] Filed: Apr. 9, 1990

[30] Foreign Application Priority Data

Apr. 10, 1989 [EP] European Pat. Off. ........ 89106272.1

[51] Int. Cl.$^5$ .............................................. A61N 5/10
[52] U.S. Cl. .............................. 250/492.3; 250/505.1; 378/65; 378/152; 378/159
[58] Field of Search .......................... 250/492.3, 505.1; 378/65, 152, 159

[56] References Cited

U.S. PATENT DOCUMENTS

| 3,582,650 | 6/1971 | Avery | 378/65 |
| 4,121,109 | 10/1978 | Taumann et al. | 250/505 |
| 4,392,239 | 7/1983 | Wilkens | 378/159 |

FOREIGN PATENT DOCUMENTS 3704795  8/1988  Fed. Rep. of Germany .

OTHER PUBLICATIONS

Medical Physics, vol. 5, No. 2, Mar.-Apr. 1982, pp. 204-207, Am. Assoc. Phys. Med., New York, U.S.; R. K. Ten Haken et al.: "The Use of Nonhydrogenous Wedge for Therapeutic Neutron Beam Shaping".
Medical Physics, vol. 5, No. 5, Sep./Oct. 1978, pp. 426-429, Am. Assoc. Phys. Med.; P. K. Kijewski et al.: "Wedge-Shaped Dose Distributions by Computer Controlled Collimator Motion".
Mevatron Users Conference Proceedings, 1983; Bengt Bjarngard, Ph. D. JCRT, Harvard Medical School, Boston, Mass.: "Computer-Controlled Radiation Therapy", European Search Report File No. EP 89 10 6272.

Primary Examiner—Jack I. Berman
Attorney, Agent, or Firm—Lawrence C. Edelman

[57] ABSTRACT

In a radiation therapy device isodose curves are adjusted both by a movable plate that is controlled during the irradiation and by a non-movable filter body in the radiation path. The filter body is located in such a manner that it has decreasing absorbability in the opening direction of the plate. On the other hand, the plate produces a decreasing effective dose in its opening direction. by superimposing the two effects, it is possible to have the isodose curve in the object of irradiation rise or fall in the opening direction, so that a wide range of variation in the possible isodose curves is obtained, without having to change the fixed filter body.

5 Claims, 2 Drawing Sheets

RADIATION THERAPY DEVICE WITH MOVEABLE APERTURE PLATE

BACKGROUND OF THE INVENTION

1. Technical Field

The present invention relates to a radiation therapy device comprising a radiation source and an aperture plate arrangement located between the radiation source and its object and defining a field of radiation.

2. Description of the Prior Art

U.S. Pat. No. 4,121,109 discloses a radiation therapy device having a aperture plate arrangement in which at least one aperture plate is movable. It has also been proposed to move the plates by a control device during irradiation in such a manner that it is possible to obtain an effective dose distribution that decreases in the open direction of the aperture plates.

From an article "Wedge-Shaped Dose Distribution by Computer-Controlled Collimator Motion" in Medical Physics (5), Sept./Oct. 1978, pages 426 to 429 it is known to use a defined plate motion to obtain a wedge-shaped isodose during irradiation. Such a wedge shaped isodose is frequently desired in radiation therapy in order to adjust to the anatomical conditions of the treatment subject. The wedge-shaped isodose results from the fact that different areas of the radiation field are exposed to irradiation for varying lengths of time. The requisite motion of the plate is caused by an iterative process.

The movable aperture plate can be regarded as a substitute for conventional wedge-shaped filters. It is also possible to obtain a wedge-shaped isodose curve by introducing a wedge-shaped filter between the radiation source and its object; however, in this case the filter has to be changed in accordance with each desired isodose curve.

On the other hand, the movable aperture plates have the disadvantage that the dose always increases in a predetermined direction, namely the one opposite to the opening direction of the plates.

SUMMARY OF THE INVENTION

It is an object of the invention to provide a radiation therapy device which has greater flexibility with respect to the achieved isodose curves that are to be employed.

According to the invention, this object is accomplished by introducing in the radiation path a non-movable filter body, in addition to the movable plate arrangement, which filter body has a decreasing absorbability in the opening direction of the plate.

By this means, it is possible to obtain an isodose curve which, for example, increases in the area to be irradiated and then decreases again. Unlike arrangements which have only an exchangeable filter body and no plate with a control device, a wide variation in the isodose curves can be obtained with this arrangement, using a single filter body.

Additional objects and features of the invention will be more readily appreciated and better understood by reference to the following detailed description which should be considered in conjunction with the drawings.

DETAILED DESCRIPTION

Figure 1:
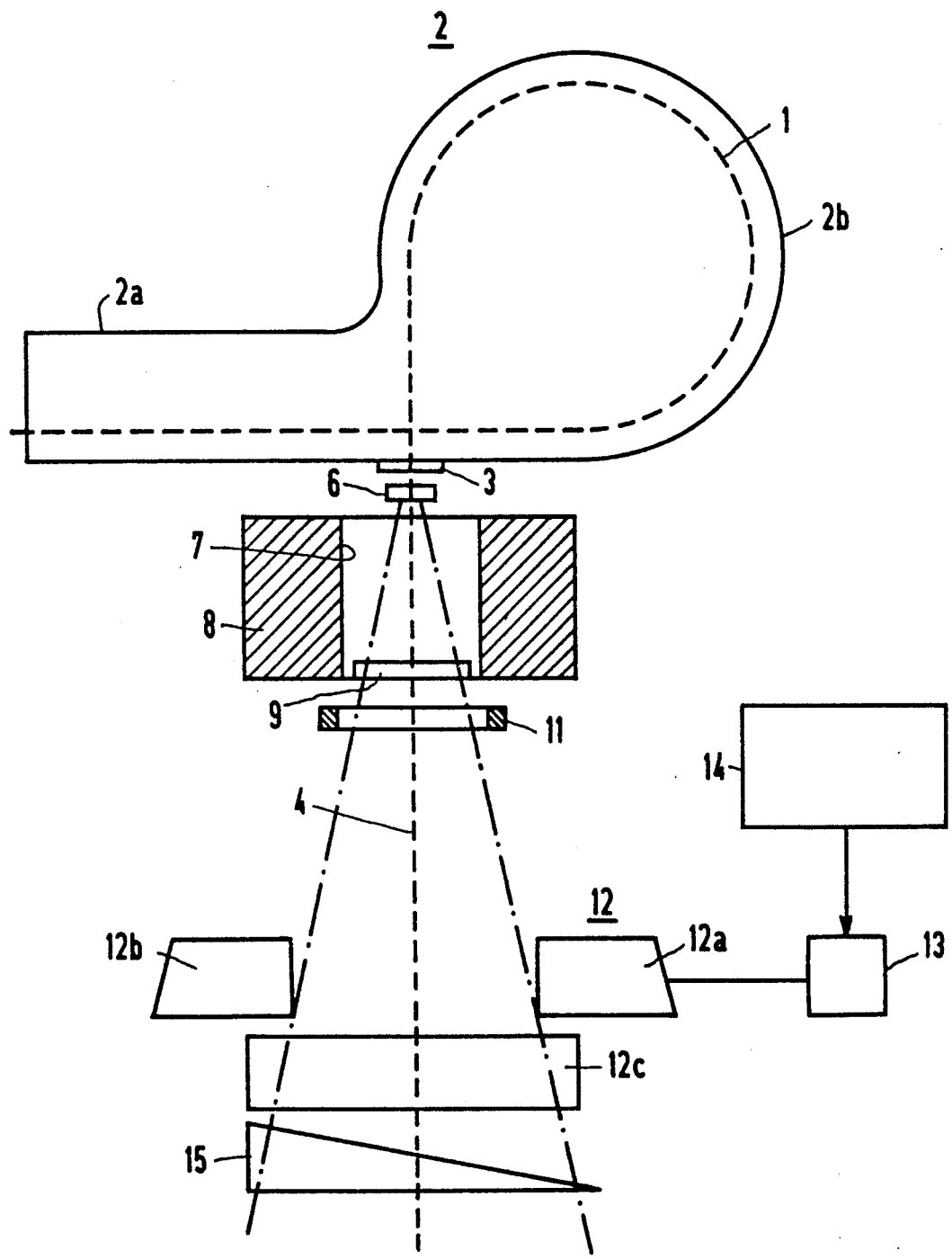
FIG. 1 depicts the schematic construction of a radiation therapy device with an electron accelerator, incorporating the principles of the invention.

The basic construction of a treatment head for a radiation therapy device is shown schematically in FIG. 1. An electron beam 1 generated in an electron accelerator 2a is guided by a guide magnet 2b onto a circular path and directed through a window 3 along an axis 4. The electron beam 1 then encounters a first scattering foil 6, goes through a passage way 7 of a shield block 8 and encounters a second scattering foil 9. Next, it is sent through a measuring chamber 11, in which the radiation dose is ascertained. If the first scattering foil 6 is replaced by a target, the electron beam may also be converted into an X-ray beam. Finally, an aperture plate arrangement 12 is provided in the path of the beam, with which the irradiated field of the subject of investigation is determined. The aperture plate arrangement 12 consists of four individual plates 12a to 12d; plate 12d cannot be seen in FIG. 1, because it is covered by plate 12c. Plates 12a to 12d produce a rectangular irradiation field.

The individual plates 12a to 12d can be adjusted by hand or with a motor. In FIG. 1 this is indicated with respect to plate 12a by a drive unit 13 which is controlled by a control unit 14. In the methods described below for determining the local dose distribution, it is assumed that at least one of plates 12a to 12d can be adjusted by means of a motor.

Finally, a wedge-shaped filter 15 is provided underneath the aperture plate arrangement 12.

The construction of a treatment head for a radiation therapy device with an electron accelerator is well known to those skilled in the art and is described, for example, in greater detail in U.S. Pat. No. 4,121,109.

It is frequently desirable in radiation therapy to have a wedge-shaped isodose curve—that is, one that has a specified angle—in which case this curve has up to now been obtained by using a wedge-shaped filter. There have, however, already been proposals to adjust the isodose curve by means of a moving plate. In the known proposals, the motion of the plate is achieved by an iterative process. The requisite motion of the plate for an angle $\alpha$ of the isodose curve can, however, also be determined analytically by means of the following equation:

$$v(x) = \frac{k}{I_o} \frac{\exp(x - B)\tan\alpha}{\mu \tan\alpha}$$

where $v(x)$ is the speed of the plate 12a, $I_0$ and k are the dose and the dose power, respectively, in open air at the depth O, B is the field width, x is the plate position, $\mu$ the effective linear attenuation coefficient and $\alpha$ the desired isodose angle. This analytic approach is possible only because in this case no scattering effects of the partial fields—that is, the fields in the individual plate positions—are taken into account.

Surprisingly enough, however, it has turned out that this leads only to negligible errors. This results from the fact that the completely opened field is weighted considerably higher in time than the growing partial fields that are opened with the moved plates. In the usual isodose curves, the largest weighing factor for a partial field is only 4% of the weighing factor for the completely open field. The analytic determination of the plate motion can be performed much more rapidly by computation than an iterative process.

Figure 2:
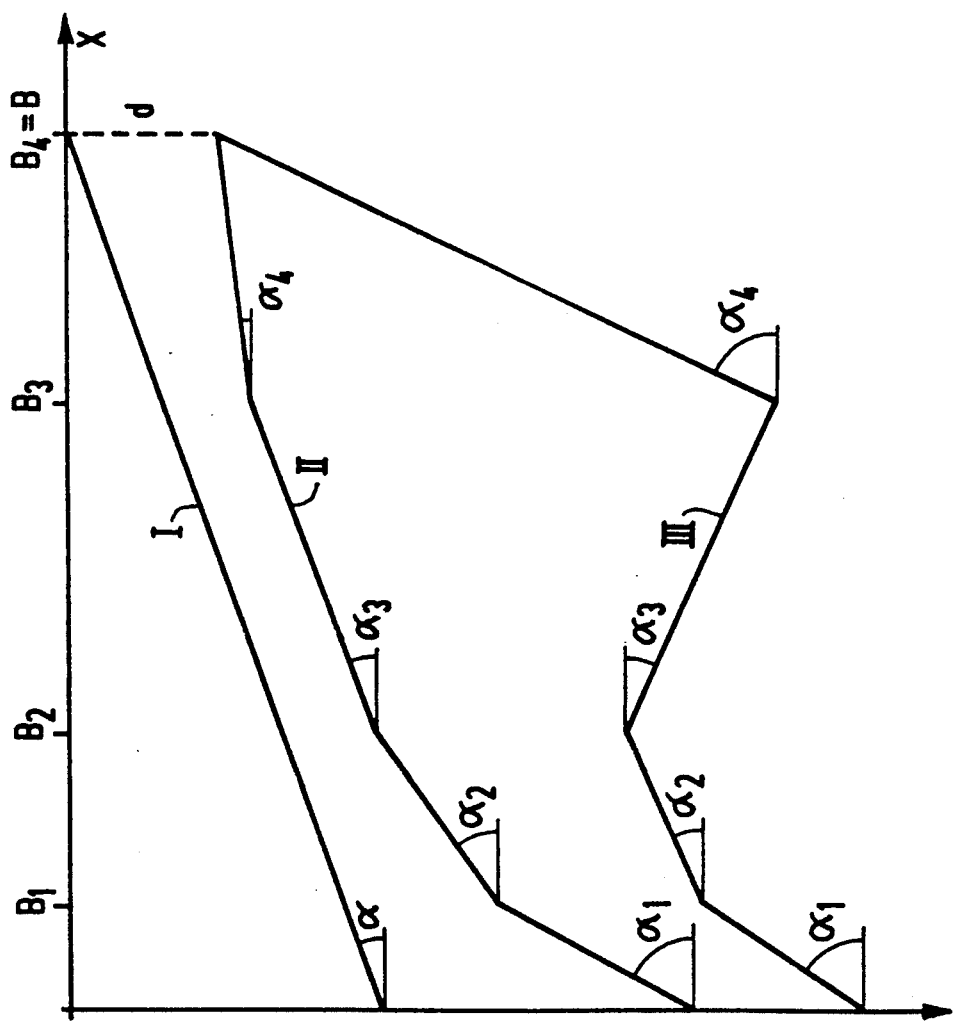
FIG. 2 illustrates various isodose curves that are obtained with the arrangement according to the invention.

Various isodose curves are shown in FIG. 2. If it is assumed that the plate 12a moves from the closed position (x=0) to the opened position (x=B), then only isodoses of the types marked I or II in FIG. 2 can be generated, that is, isodoses with $\tan\alpha > 0$. Specifically, we have:

$$I(x) = I_O \exp(-\mu x \tan\alpha),$$

since $I(x) < I_O$ and $x, \mu > 0$ the result is that $\tan\alpha \geq 0$ and $0° \leq \alpha \leq 90°$.

Figure 3:
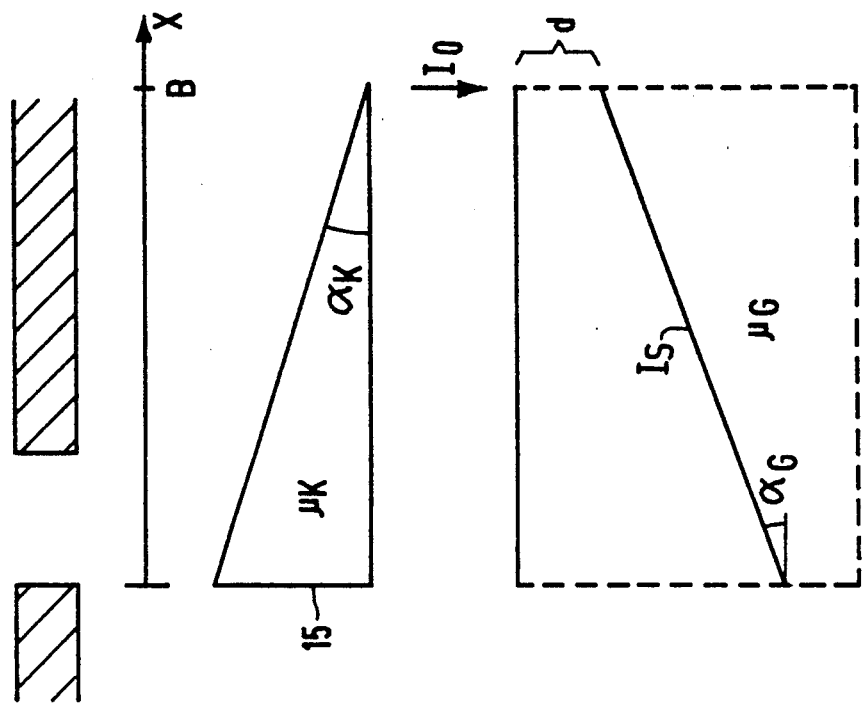
FIG. 3 is a schematic arrangement of a plate, a filter body and the body of a treatment subject.

This implies a limitation on the available isodose curves, which limitation can be overcome with the following arrangement described with the aid of FIG. 3. In this case, the effect of a real wedge-shaped filter 15 with a fixed angle $\alpha_K$ and an attenuation coefficient $\mu_K$ is superimposed on the system including the irradiation object and the aperture plate arrangement 12. In this case, $\alpha$ can also be negative. In principle, the filter can have any desired shape; the only condition that must be fulfilled is that the beam absorption decreases as the value of x increases (i.e., in the open direction of the plate 12a).

Below, we consider the configuration for a wedge-shaped filter with an angle $\alpha_K$. For the dose value $I(x)$, we have:

$$I(x) = I_S \exp\{\mu_G[d+(B-X)\tan\alpha_G]\cdot\exp[\mu_K(B-X)\tan\alpha_K]\}$$

where $I_S$ is the value of the isodose which is to travel at the depth d within the angle $\alpha_G$. Here the index G stands for tissue.

For the open-air dose $I_O$ at the level of the body surface (without the effect of the plate 12a and the filter 15), we have:

$$I_O = I_S \exp[\mu_G(d+B\tan\alpha_G) + \mu_K B \tan\alpha_K)]$$

From which we obtain:

$$I(x) = I_o \exp[-x(\mu_G \tan\alpha_G + \mu_K \tan\alpha_K)]$$

By analogy with the considerations set forth above, the following relationship must apply:

$$\mu_G \tan\alpha_G + \mu_K \tan\alpha_K \geq 0$$

As a result, we have:

$$\tan\alpha_G \geq \frac{\mu_K}{\mu_G} \tan\alpha_K$$

This defines the range of the possible isodose angle $\alpha_G$, and it is evident that both positive and negative values are possible.

For the situation in which the isodose is to have only the constant angle $\alpha_G$, we can derive the following motion equation:

$$x(t) = \frac{\ln\frac{k}{I_o}(T + t_c - t)}{\mu_G \tan\alpha_G + \mu_K \tan\alpha_G}$$

The motion equation given for an isodose with a constant angle $\alpha_G$ can also be generalized for the situation in which the isodose has a number of different angle segments $\alpha_i$ for the coordinates x. For the range i, the following motion equation applies:

$$x_i(t) = -\frac{\ln\frac{k}{I_o}(T + t_c - t) + \mu \sum_{i=1}^{i} B_{i-1}(\tan\alpha_{i-1} - \tan\alpha_i)}{\mu \tan\alpha_i + \mu_K \tan\alpha_K}$$

$$v_i(x) = \frac{k}{I_o} \frac{\exp\left[(x - B_{i-1})(\mu \tan\alpha_i + \mu_K \tan\alpha_K) + \sum_{i=2}^{i=1}(B_{i-1} - B_{i-2})(\mu \tan\alpha_i + \mu_K \tan\alpha_K)\right]}{\mu \tan\alpha_i + \mu_K \tan\alpha_K}$$

For the case in which it is desired to generate isodoses that increase only in the x-direction, the real wedge-shaped filter 15 can be dispensed with, and the above equation is simplified, with $\tan\alpha_K = 0$ and $\mu_K = 0$.

The use, described above, of a computer-controlled plate with the simultaneous introduction of a real wedge-shaped filter 3 permits a wide variation in the specification of the isodose curve, with the option of obtaining increasing doses in the opening direction of the plate. There is no way in which a dose curve of this kind can be obtained with movable plates alone. In principle it would be possible to establish more complex isodose curves by means of filters alone but in view of the great number of special filter shapes required, this is not practical. However, with the combination of a movable plate and real wedge-shaped filter as presented here, a wide range of variation in the determination of isodoses is obtainable, even with a single wedge-shaped filter and even for several different angle segments.

Even for complicated isodose curves, the motion equation for the plate can be obtained by purely analytic methods; in other words, time-consuming iterative computation processes are not required.

There has thus been shown and described a novel radiation therapy device which fulfills all the objects and advantages sought for. Many changes, modifications, variations and other uses and applications of the subject invention will, however, become apparent to those skilled in the art after considering the specification and the accompanying drawings which disclose an embodiment thereof. All such changes, modifications, variations and other uses and applications which do not depart from the spirit and scope of the invention are deemed to be covered by the invention which is limited only by the claims which follow.

I claim:

1. A radiation therapy device for irradiating an object with a radiation beam, said radiation therapy device comprising:
   a radiation source for generating said radiation beam,
   an aperture plate arrangement located in said radiation beam between said radiation source and said object and including a plurality of plates for determining a radiation field at said object,
   a control device for moving at least one plate in said aperture plate arrangement during irradiation in such a manner that an effective dose decreasing in the opening direction of said plate is obtained in said radiation field,
   a filter body having a decreasing absorbability in the opening direction of said plate, and
   means for placing said filter body in said radiation beam between said radiation source and said object.

2. A radiation therapy device according to claim 1, wherein the radiation source comprises an electron accelerator and a guide magnet.

3. A radiation therapy device according to claim 1, wherein the filter body is wedge-shaped.

4. A radiation therapy device according to claim 1, wherein said control device moves said at least one plate so that an isodose angle generated is set at various levels for different areas of the radiation field.

5. A radiation therapy device according to claim 1, wherein said control device moves said at least one plate according to the following equation:

$$x(t) = \frac{\ln \frac{k}{I_o}(T + tc - t) + \mu \sum_{i=1}^{i} B_{i-1}(\tan\alpha_{i-1} - \tan\alpha_i)}{\mu \tan\alpha_i + \mu_K \tan\alpha_K}$$

where:
   $x$ = x-coordinate of the plate 12a
   $K$ = effective dose in open air at the depth O
   $I_o$ = dose in open air at the depth O
   $T$ = time in which the plate (12a) moves from the closed position to the open position
   $tc$ = time during which the radiation is transmitted when the plate is fully open
   $\mu$ = effective linear attenuation coefficient
   $B_i$ = x-coordinate at the end of an angle segment
   $\alpha_i$ = isodose angle in the respective segment
   $\alpha_K$ = angle of the real filter body
   $\mu_K$ = attenuation coefficient of the real filter body The index i designates a segment with a constant isodose angle $\alpha_i$.

* * * * *